US010918770B2

(12) United States Patent
Fewkes et al.

(10) Patent No.: US 10,918,770 B2
(45) Date of Patent: Feb. 16, 2021

(54) VACUUM ASSISTED WOUND CLOSURE ASSEMBLY AND METHODS OF IRRADIATING A WOUND USING THE SAME

(71) Applicant: Corning Incorporated, Corning, NY (US)

(72) Inventors: Edward John Fewkes, Corning, NY (US); Stephan Lvovich Logunov, Corning, NY (US); Cynthia Jean Wilson, Corning, NY (US)

(73) Assignee: CORNING INCORPORATED, Corning, NY (US)

( * ) Notice: Subject to any disclaimer, the term of this patent is extended or adjusted under 35 U.S.C. 154(b) by 843 days.

(21) Appl. No.: 15/203,102

(22) Filed: Jul. 6, 2016

(65) Prior Publication Data

US 2017/0232161 A1 Aug. 17, 2017

Related U.S. Application Data

(60) Provisional application No. 62/294,614, filed on Feb. 12, 2016.

(51) Int. Cl.
*A61M 35/00* (2006.01)
*A61F 13/02* (2006.01)
(Continued)

(52) U.S. Cl.
CPC ..... *A61M 1/0088* (2013.01); *A61F 13/00068* (2013.01); *A61F 13/0216* (2013.01);
(Continued)

(58) Field of Classification Search
CPC ............ A61F 13/00; A61F 13/02; A61F 8/44; A61M 1/00; A61M 3/00; A61M 31/00
See application file for complete search history.

(56) References Cited

U.S. PATENT DOCUMENTS 5,636,643 A * 6/1997 Argenta .............. A61M 1/0088
128/897
6,551,346 B2 4/2003 Crossley
(Continued)

FOREIGN PATENT DOCUMENTS

| CN | 204840698 U | 12/2015 |
|---|---|---|
| CN | 106178280 A | 12/2016 |

(Continued)

OTHER PUBLICATIONS

Hamblin et al.; "Mechanisms of Low Level Light Therapy"; Proc. of SPIE, vol. 6140, 614001, (2006); pp. 1-12.
(Continued)

*Primary Examiner* — Tatyana Zalukaeva
*Assistant Examiner* — Ilya Y Treyger (57) ABSTRACT

A method of irradiating a wound that includes positioning a wound insertion foam within a wound cavity of a wound and covering the wound insertion foam using a wound sealing layer. The method further includes pumping fluid from the wound cavity using a drain tube sealed within the wound cavity and coupled to a vacuum source, and irradiating the wound using a light diffusing optical fiber that is optically coupled to a therapeutic light source and includes light scattering structures distributed along the light diffusing optical fiber. A portion of the light diffusing optical fiber is positioned within a wound tissue region of the wound, the wound cavity, or both, such that light emitted by the therapeutic light source enters the light diffusing optical fiber, scatters outward from the light diffusing optical fiber, and irradiates the wound tissue region, a wound cavity surface of the wound, or both.

17 Claims, 4 Drawing Sheets

(51) Int. Cl.
*A61M 1/00* (2006.01)
*A61N 5/06* (2006.01)
*A61M 27/00* (2006.01)
*A61F 13/00* (2006.01)
*A61M 3/00* (2006.01)
*A61M 21/00* (2006.01)
*A61B 18/22* (2006.01)

(52) U.S. Cl.
CPC ........ *A61M 1/0066* (2013.01); *A61M 1/0098* (2014.02); *A61M 27/00* (2013.01); *A61N 5/0616* (2013.01); *A61N 5/0624* (2013.01); A61B 2018/2244 (2013.01); A61B 2018/2261 (2013.01); A61F 2013/0054 (2013.01); A61F 2013/0074 (2013.01); A61F 2013/00536 (2013.01); A61F 2013/00919 (2013.01); A61M 2205/051 (2013.01); A61M 2205/587 (2013.01); A61N 2005/063 (2013.01); A61N 2005/0645 (2013.01)

(56) References Cited

U.S. PATENT DOCUMENTS

| | | | |
|---|---|---|---|
| 6,994,702 B1 | 2/2006 | Johnson | |
| 8,404,273 B2 | 3/2013 | Baumgart et al. | |
| 8,585,681 B2 | 11/2013 | Boenig et al. | |
| 8,779,386 B2 | 7/2014 | Bak | |
| 8,980,174 B2 | 3/2015 | Haytman et al. | |
| 9,039,966 B2 | 5/2015 | Anderson et al. | |
| 9,067,059 B2 | 6/2015 | Bissig et al. | |
| 9,259,513 B2 | 2/2016 | Bedwell et al. | |
| 9,278,148 B2 | 3/2016 | Fewkes et al. | |
| 9,393,339 B2 | 7/2016 | Park et al. | |
| 9,439,989 B2 | 9/2016 | Lalicki et al. | |
| 9,550,005 B2 | 1/2017 | Lin et al. | |
| 9,795,466 B2 | 10/2017 | Piergallini et al. | |
| 9,808,647 B2 | 11/2017 | Rhodes et al. | |
| 9,925,390 B2 | 3/2018 | Yehezkel | |
| 9,943,379 B2 | 4/2018 | Gregg, II et al. | |
| 10,046,070 B1 | 8/2018 | Zaborsky et al. | |
| 10,166,402 B2 | 1/2019 | Brennan et al. | |
| 10,183,144 B2 | 1/2019 | Tang et al. | |
| 10,241,035 B2 | 3/2019 | Bonnick et al. | |
| 2006/0085052 A1 | 4/2006 | Feuerstein et al. | |
| 2008/0215020 A1 | 9/2008 | Reeves et al. | |
| 2008/0281383 A1* | 11/2008 | Butler | A61N 5/0616 607/80 |
| 2009/0257910 A1 | 10/2009 | Segal | |
| 2010/0268151 A1 | 10/2010 | Mauge et al. | |
| 2013/0035629 A1 | 2/2013 | Soltz et al. | |
| 2013/0116612 A1 | 5/2013 | Stephan | |
| 2015/0080709 A1 | 3/2015 | Chaturvedi | |
| 2015/0148734 A1 | 5/2015 | Fewkes et al. | |
| 2018/0036443 A1 | 2/2018 | Messerly | |
| 2018/0147417 A1 | 5/2018 | Rantala | |
| 2018/0178031 A1 | 6/2018 | Wu | |
| 2018/0207302 A1 | 7/2018 | Vasilenko | |
| 2018/0304094 A1 | 10/2018 | Hicks et al. | |
| 2018/0326104 A1 | 11/2018 | Hawkins et al. | |

FOREIGN PATENT DOCUMENTS

| | | |
|---|---|---|
| CN | 106178282 A | 12/2016 |
| CN | 105396169 B | 6/2018 |
| CN | 108671243 A | 10/2018 |
| JP | 05546575 B2 | 7/2014 |
| KR | 1362704 B1 | 2/2014 |
| KR | 1851576 B1 | 4/2018 |
| KR | 2018049757 A | 5/2018 |
| KR | 1892996 B1 | 8/2018 |
| KR | 2018135256 A | 12/2018 |
| KR | 2018135257 A | 12/2018 |
| WO | 2000059424 A1 | 10/2000 |
| WO | 2015168129 A1 | 11/2015 |
| WO | 2018009864 A1 | 1/2018 |
| WO | 2019025808 A1 | 2/2019 |

OTHER PUBLICATIONS

World Wide Wounds; "An Introduction to the Use of Vacuum Assisted Closure"; Retrieval Date: Jun. 28, 2016; http://www.worldwidewounds.com/2001/may/Thomas/Vacuum-Assisted-Closure.html; pp. 1-4.

Chung et al.; "The Nuts and Bolts of Low-Level Laser (Light) Therapy"; Annals of Biomedical Engineering, vol. 40, No. 2 (Feb. 2012); pp. 516-533.

FDA U.S. Food and Drug Administration; "Update on Serious Complications Associated with Negative Pressure Would Therapy Systems: FDA Safety Communication"; Date Issued: Feb. 24, 2011; http://www.fda.gov/MedicalDevices/Safety/AlertsandNotices/ucm244211.htm.

International Search Report and Written Opinion PCT/US2017/017399 Dated Apr. 21, 2017.

* cited by examiner

VACUUM ASSISTED WOUND CLOSURE ASSEMBLY AND METHODS OF IRRADIATING A WOUND USING THE SAME

This application claims the benefit of priority under 35 U.S.C. § 119 of U.S. Provisional Application Ser. No. 62/294,614, filed on Feb. 12, 2016, the content of which is relied upon and incorporated herein by reference in its entirety.

BACKGROUND

The present disclosure relates to vacuum assisted wound closure assemblies. More specifically, the present disclosure introduces technology for vacuum assisted wound closure assemblies having one or more light diffusing optical fibers.

BRIEF SUMMARY

According to the subject matter of the present disclosure, a method of irradiating a wound includes positioning a wound insertion foam within a wound cavity of a wound and covering the wound insertion foam positioned within the wound cavity using a wound sealing layer having a sealing surface, such that the sealing surface seals the wound insertion foam within the wound cavity. The method further includes pumping fluid from the wound cavity using a drain tube including a drainage end fluidly coupled to the wound insertion foam and sealed within the wound cavity using the wound sealing layer and a vacuum end fluidly coupled to a vacuum source, and irradiating the wound using a light diffusing optical fiber optically coupled to a therapeutic light source. The light diffusing optical fiber includes one or more light scattering structures distributed along at least a treatment length of the light diffusing optical fiber. Further, at least a portion of the treatment length of the light diffusing optical fiber is positioned within a wound tissue region of the wound, the wound cavity, or both, such that at least a portion of light emitted by the therapeutic light source enters the light diffusing optical fiber, scatters outward from the light diffusing optical fiber, and irradiates the wound tissue region, a wound cavity surface of the wound, or both.

In accordance with one embodiment of the present disclosure, a method of irradiating a wound includes positioning a wound insertion foam within a wound cavity of a wound and covering the wound insertion foam positioned within the wound cavity using a wound sealing layer comprising a sealing surface, such that the sealing surface seals the wound insertion foam within the wound cavity. The method further includes pumping fluid from the wound cavity using a drain tube having a drainage end fluidly coupled to the wound insertion foam and a vacuum end fluidly coupled to a vacuum source, the drainage end extending into a vacuum entry port that extends through the wound sealing layer such that the drainage end of the drain tube is fluidly coupled to the wound insertion foam and sealed within the wound cavity using the wound sealing layer and irradiating the wound using a light diffusing optical fiber optically coupled to a therapeutic light source using a transmission optical fiber that extends the light diffusing optical fiber and the therapeutic light source. The light diffusing optical fiber comprises one or more light scattering structures distributed along at least a treatment length of the light diffusing optical fiber. A portion of the light diffusing optical fiber extends within the drain tube and extends through the vacuum entry port. Further, at least a portion of the treatment length of the light diffusing optical fiber is positioned within a wound tissue region of the wound at a depth less than a wound depth extending from a wound cavity surface of the wound cavity, such that at least a portion of light emitted by the therapeutic light source enters the light diffusing optical fiber, scatters outward from the light diffusing optical fiber, and irradiates the wound tissue region of the wound.

In accordance with another embodiment of the present disclosure, a vacuum assisted wound closure assembly includes a wound insertion foam, a wound sealing layer, a drain tube, a vacuum source, a light diffusing optical fiber, a transmission optical fiber, and a therapeutic light source. The wound insertion foam is positionable within a wound cavity of a wound. The drain tube includes a drainage end fluidly coupled to the wound insertion foam and a vacuum end fluidly coupled to the vacuum source. The transmission optical fiber is positioned between and optically coupled to the light diffusing optical fiber and the therapeutic light source, extends a transmission length, and optically couples the light diffusing optical fiber to the therapeutic light source. The light diffusing optical fiber includes a plurality of light scattering structures distributed along at least a treatment length of the light diffusing optical fiber. Further, the wound sealing layer includes a sealing surface configured to seal the wound insertion foam, the drainage end of the drain tube, and at least a portion of the light diffusing optical fiber within the wound cavity when the wound insertion foam is positioned within the wound cavity.

Although the concepts of the present disclosure are described herein with primary reference to some specific vacuum assisted wound closure assembly configurations, it is contemplated that the concepts will enjoy applicability to vacuum assisted wound closure assemblies having any configuration.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
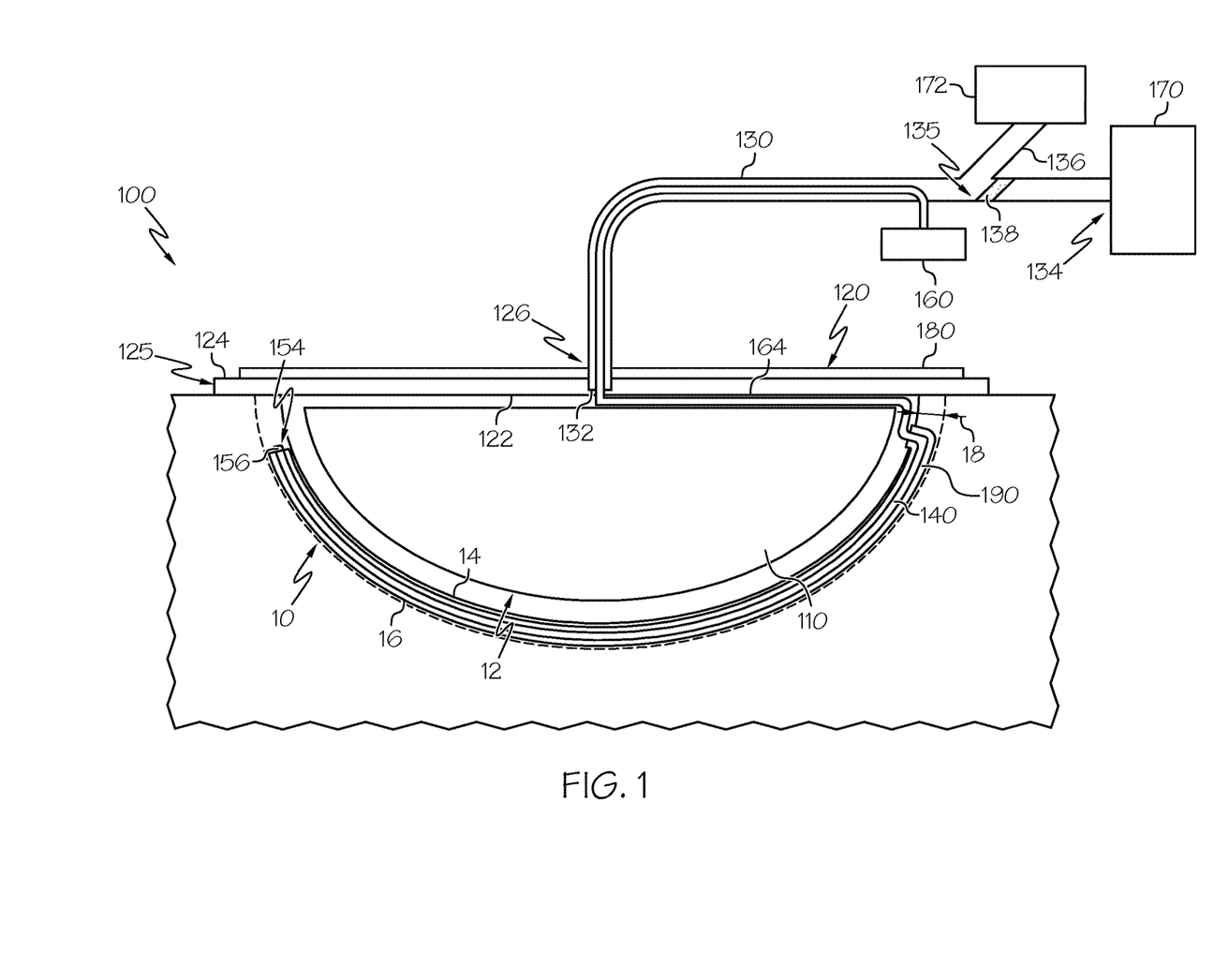
FIG. 1 is a schematic illustration of a vacuum assisted wound closure assembly having a light diffusing optical fiber extending into a wound, according to one or more embodiments shown and described herein.

FIG. 1 is a schematic illustration of a vacuum assisted wound closure assembly 100. The vacuum assisted wound closure assembly 100 comprises a wound insertion foam 110, a wound sealing layer 120, a drain tube 130, a vacuum source 170, a light diffusing optical fiber 140, a transmission optical fiber 164, and a therapeutic light source 160. The vacuum assisted wound closure assembly 100 may be used to pump fluid from a wound 10 using the drain tube 130 and the vacuum source 170 and may be used to irradiate the wound 10 using the light diffusing optical fiber 140 and the therapeutic light source 160.

The wound insertion foam 110 may comprise any foam material, for example, reticulated open cell foam, and is positionable within a wound cavity 12 of the wound 10. The drain tube 130 comprises a drainage end 132 fluidly coupled to the wound insertion foam 110 and a vacuum end 134 fluidly coupled to the vacuum source 170. For example, the drainage end 132 may extend into the wound cavity 12 when the wound insertion foam 110 is positioned within the wound cavity 12 and the vacuum end 134 may be coupled to the vacuum source 170. The vacuum source 170 may comprise any fluid pump structurally configured to generate suction within the drain tube 130, for example, generate fluid flow from the drainage end 132 to the vacuum end 134 of the drain tube 130.

Referring still to FIG. 1, a fluid collection vessel 172 may be fluidly coupled to the drain tube 130. The fluid collection vessel 172 may comprise any container configured to house fluid, for example, fluid removed from the wound 10. The drain tube 130 may comprise a collection branch 136 extending from the drain tube 130 at a branching location 135 and terminating at the fluid collection vessel 172. Further, a fluid separating mesh 138 may be positioned within the drain tube 130 at a location fluidly downstream from the branching location 135, for example, between the branching location 135 and the vacuum source 170. The fluid separating mesh 138 may comprise any filter material. In operation, the fluid separating mesh 138 may inhibit non-gaseous fluid from traversing the fluid separating mesh 138 and may direct non-gaseous fluid into the collection branch 136. Further, the fluid collection vessel 172 may be positioned within or coupled to the vacuum source 170.

Figure 2:
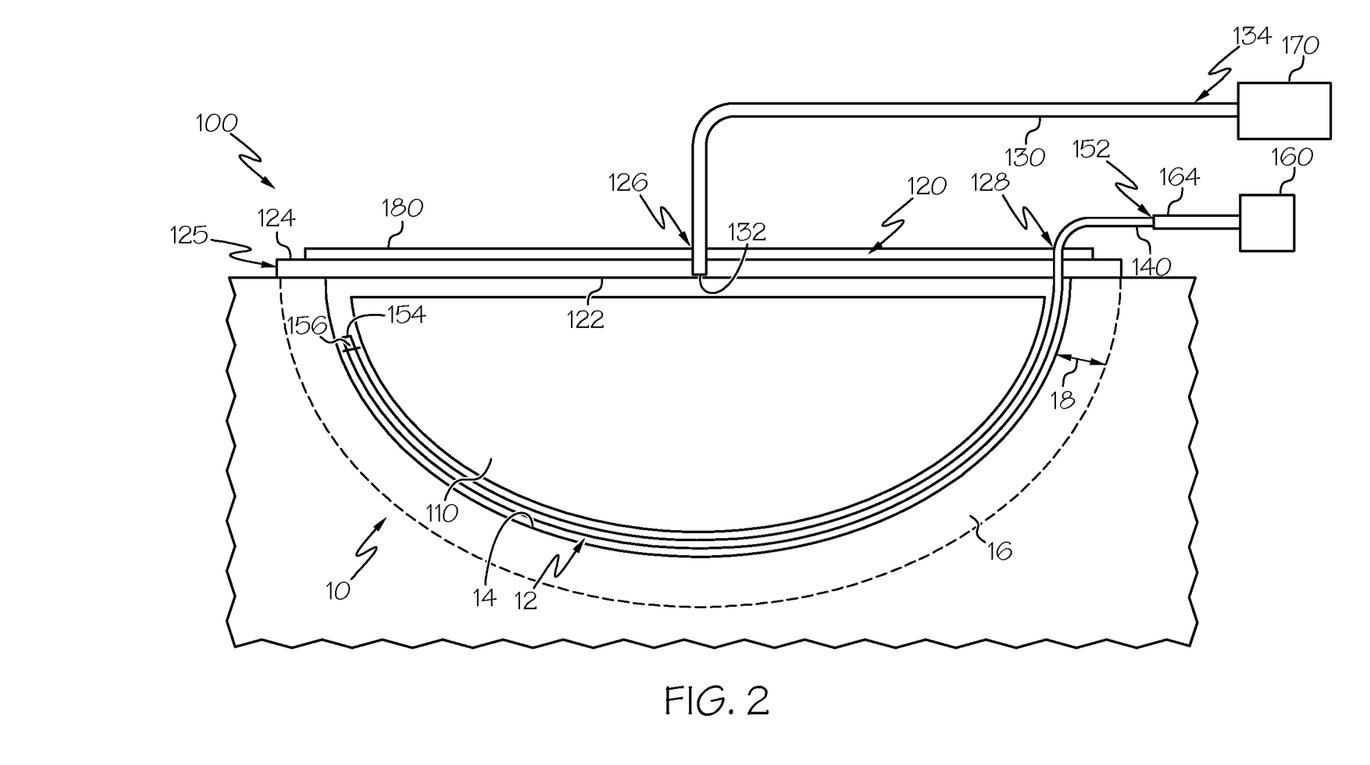
FIG. 2 is a schematic illustration of another vacuum assisted wound closure assembly having a light diffusing optical fiber extending into a wound, according to one or more embodiments shown and described herein.

Referring now to FIGS. 1 and 2, the wound sealing layer 120 comprises a sealing surface 122 opposite an outward surface 124. The wound sealing layer 120 is configured to seal the wound insertion foam 110, the drainage end 132 of the drain tube 130 within the wound cavity 12, for example, when the wound insertion foam 110 is positioned within wound cavity 12. Further, the wound sealing layer 120 may also seal at least a portion of the light diffusing optical fiber 140 within the wound cavity 12 such that the light diffusing optical fiber 140 may emit light into the wound cavity 12. The wound sealing layer 120 may comprise an adhesive material disposed on the sealing surface 122, for example, along a sealing perimeter 125 of the wound sealing layer 120. The adhesive material may comprise a pressure sensitive adhesive, an acrylic adhesive, or a combination thereof.

The wound sealing layer 120 may comprise an elastomeric material. Further, the wound sealing layer 120 may be fluidically semi-permeable such that some or all gases, for example, oxygen, may traverse the wound sealing layer 120. Moreover, the wound sealing layer 120 may be opaque such that at least some light emitted into the wound cavity 12 by the light diffusing optical fiber 140 is inhibited from traversing the wound sealing layer 120. For example, it may be advantageous for the wound sealing layer 120 to be opaque when the light diffusing optical fiber 140 emits ultraviolet light. Further, an opaque layer 180 may be coupled to the wound sealing layer 120, for example, to the outward surface 124 and/or the sealing surface 122 of the wound sealing layer 120 such that such that at least some light emitted into the wound cavity 12 by the light diffusing optical fiber 140 is inhibited from traversing the opaque layer 180.

Referring still to FIGS. 1 and 2, a vacuum entry port 126 extends through the wound sealing layer 120. The drain tube 130 may extend into the vacuum entry port 126, for example, through the vacuum entry port 126, such that the drainage end 132 of the drain tube 130 is fluidly coupled to the wound insertion foam 110. The light diffusing optical fiber 140 may extend within the drain tube 130 and extend through the vacuum entry port 126. Further, the light diffusing optical fiber 140 may extend through the vacuum entry port 126, adjacent the drain tube 130. Moreover, the wound sealing layer 120 may comprise a fiber entry port 128 extending through the wound sealing layer 120 at a location apart from the vacuum entry port 126 and the light diffusing optical fiber 140 may extend through the fiber entry port 128 and into the wound cavity 12.

Figure 3:
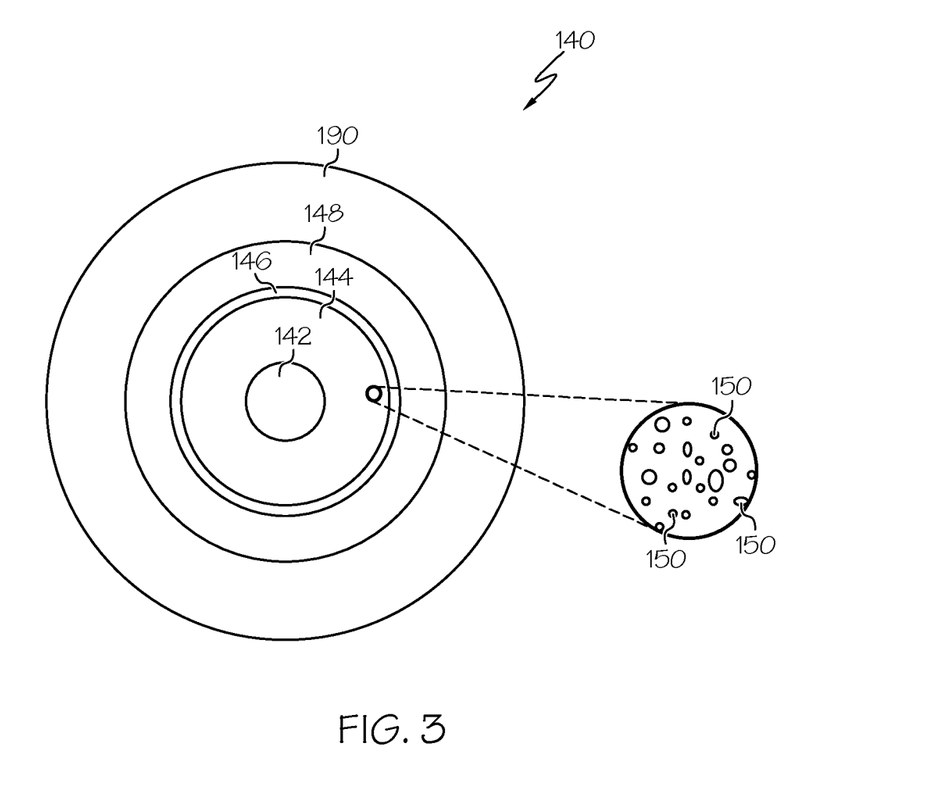
FIG. 3 is a cross-sectional schematic illustration of the light diffusing optical fiber of FIGS. 1 and 2, according to one or more embodiments shown and described herein.

Referring now to FIGS. 1-3, the light diffusing optical fiber 140 is optically coupled to the therapeutic light source 160. The therapeutic light source 160 may comprise any light source structurally configured to emit light, for example, a laser light source, a light emitting diode (LED), an ultraviolet light source, such as an ultraviolet LED, an ultraviolet lamp, or the like. Further, the vacuum assisted wound closure assembly 100 may comprise additional light sources, for example, a second therapeutic light source 162 (FIG. 4) such that the light diffusing optical fiber 140 may be selectively optically coupled to different light sources outputting different wavelengths of light.

In operation, the therapeutic light source 160 may emit light comprising a wavelength between about 250 nm and about 1100 nm, for example 250 nm, 350 nm, 405 nm, 445 nm, 530 nm, 630 nm, 650 nm, 700 nm, between about 780 nm and about 980 nm, or the like. For example, the therapeutic light source 160 may emit light at wavelengths that activate, alter, or otherwise react with one or more photo-active pharmaceuticals. For example, Photofrin™ may be activated by emitted light having wavelengths between about 600 nm and about 680 nm, or wavelengths near UV wavelengths, such as between about 370 nm and about 420 nm Further, the therapeutic light source 160 may emit a pulsed light. For example, the pulsed light may be pulsed at frequency within a treatment frequency range comprising between about 70 Hz and 80 Hz, between about 145 Hz and 155 Hz, between about 290 Hz and 300 Hz, between about 585 Hz and 595 Hz, between about 1170 Hz and about 1180 Hz, between about 2345 Hz and about 2355 Hz, or between about 4695 Hz and about 4705 Hz. Further, the treatment frequency range may encompass one or more of the Noiger frequencies, for example, 73 Hz, 147 Hz, 294 Hz, 587 Hz, 1174 Hz, 2349 Hz, 4698 Hz, or the like.

As depicted in FIG. 2, a transmission optical fiber 164 may be positioned between and optically coupled to the light diffusing optical fiber 140 and the therapeutic light source 160. The transmission optical fiber 164 may extend a transmission length and may optically couple the light diffusing optical fiber 140 to the therapeutic light source 160. The transmission optical fiber 164 may comprise any optical fiber that provides a light propagation pathway along the transmission length and at least partially inhibits radial emission of light along the transmission length.

Referring now to FIG. 3, the light diffusing optical fiber 140 comprises a plurality of light scattering structures 150 distributed along a treatment length of the light diffusing optical fiber 140. As used herein, the treatment length refers to the length of the light diffusing optical fiber 140 comprising the plurality of light scattering structures 150. The treatment length may extend along the entire length of the light diffusing optical fiber 140 or may extend along a portion of the length of the light diffusing optical fiber 140. The light diffusing optical fiber 140 may comprise a glass fiber, for example, silica, a plastic fiber, or the like. Further, the light diffusing optical fiber 140 may comprise a diameter between about 100 µm and about 500 µm, for example, about 200 µm, about 250 µm, about 300 µm, or the like, and may comprise a bend radius between about 5 mm and about 15 mm. for example, 7 mm, 10 mm, 12 mm, or the like.

As depicted in FIG. 3, the light diffusing optical fiber 140 includes a core 142, a cladding layer 144 encircling the core 142, and may also include a coating layer 146 encircling the cladding layer 144. The coating layer 146 may comprise a transparent medical grade polymer, a medical grade plastic, a plurality of photo-active sterilization molecules, a cross-linked coating, or a combination thereof. For example, the medical grade plastic may comprise silicone and the plurality of photo-active sterilization molecules may comprise rutile $TiO_2$. Further, at least a portion of the treatment length of the light diffusing optical fiber 140 may extend within a fiber housing catheter 190 that comprises an optically transmissive material, as depicted in FIG. 2.

The one or more light scattering structures 150 may be positioned within the core 142, the cladding layer 144, or both. Further, the one or more light scattering structures 150 are structurally configured such that the light diffusing optical fiber 140 emits light radially along the treatment length of the light diffusing optical fiber 140 when the therapeutic light source 160 emits light. For example, the light diffusing optical fiber 140 may radially emit light at a scattering induced attenuation loss comprising between about 0.1 dB/m and about 100 dB/m, for example, at about 0.5 dB/m, 1 dB/m, 5 dB/m, 10 dB/m, 25 dB/m, 50 dB/m, 75 dB/m, or the like.

Referring still to FIG. 3, the one or more light scattering structures 150 may comprise a plurality of gas filled voids or other nano-sized structures positioned within the core 142, the cladding layer 144, or both. The plurality of gas filled voids may be uniformly or non-uniformly distributed along the treatment length of the light diffusing optical fiber 140. In operation, the plurality of gas filled voids scatter a portion of the light traversing the treatment length of the light diffusing optical fiber 140 outward from the light diffusing optical fiber 140. The plurality of gas filled voids may be positioned within the light diffusing optical fiber 140 such that a cross section of the light diffusing optical fiber 140 may contain 50 or more gas filled voids, for example, 75 or more, 100 or more, or 200 or more. In operation, an increased number of gas filled voids positioned within the light diffusing optical fiber 140 may generate an increased scattering induced attenuation loss when light traverses the light diffusing optical fiber 140. Further, the plurality of gas filled voids may house any gas, for example, $SO_2$, Kr, Ar, $CO_2$, $N_2$, $O_2$ or a mixture thereof. Moreover, the cross-sectional size (e.g., diameter) of each of the plurality of gas filled voids may be between about 10 nm and about 1 µm, for example, between about 15 nm and about 500 nm, or the like.

The one or more light scattering structures 150 may also comprise a refractive coating optically coupled to a core 142 of the light diffusing optical fiber 140. The refractive coating may be positioned on the cladding layer 144, for example, encircling or intermittently positioned on the cladding layer 144 or may be positioned directly on the core 142, for example, encircling or intermittently positioned on the core 142. Further, the coating layer 146 may comprise the refractive coating, the refractive coating may be positioned between the cladding layer 144 and the coating layer 146, the refractive coating may encircle the coating layer 146, or the refractive coating may be intermittently positioned on the coating layer 146.

Further, the refractive coating comprises an index of refraction that is greater than an index of refraction of the core 142 and the index of refraction of the cladding layer 144 such that at least partial refraction may occur at the optical interface formed between the refractive coating and the core 142, cladding layer 144, or the like, such that at least a portion of light traversing the core 142 exits the core 142, traverses the refractive coating, and scatters outward from the light diffusing optical fiber 140. The refractive coating may comprise any material having a higher index of refraction than the material of the core 142, such as $GeO_2$, $TiO_2$, $ZrO_2$, ZnO, BaS, alumina, or the like. For example, these higher index of refraction materials (e.g., $GeO_2$, $TiO_2$, $ZrO_2$, ZnO, BaS, alumina, or the like) may be particles (e.g., light scattering particles) dispersed within the refractive coating. Further, the light scattering particles may comprise a cross-sectional length, (e.g., diameter in embodiments comprising spherical particles) of between about 100 nm and about 2 µm, e.g., 250 nm, 500 nm, 750 nm, 1 µm, 1.5 µm, or the like. Moreover, the one or more light scattering structures 150 may comprise inks that include scattering pigments or molecules, such as $TiO_2$ positioned on or within the light diffusing optical fiber 140. Other light scattering structures may include surface defect regions on the core 142, the cladding layer 144, or both.

As depicted in FIG. 3, the light diffusing optical fiber 140 may also include a fiber jacket 148 encircling the coating layer 146. The fiber jacket 148 may comprise a transparent medical grade polymer, a cross-linked coating, or a combination thereof. A portion of the fiber jacket 148 may be opaque such that light does not emit radially along the opaque portion of the fiber jacket 148.

Referring again to FIGS. 1 and 2, the light diffusing optical fiber 140 may comprise a source end 152 optically coupled to the therapeutic light source 160 and a termination end 154 opposite the source end 152. As depicted in FIGS. 1 and 2, a reflector cap 156 may be coupled to the termination end 154 of the light diffusing optical fiber 140. Alternatively, the termination end 154 may be optically coupled to a second therapeutic light source 162 as depicted in FIG. 4.

Figure 4:
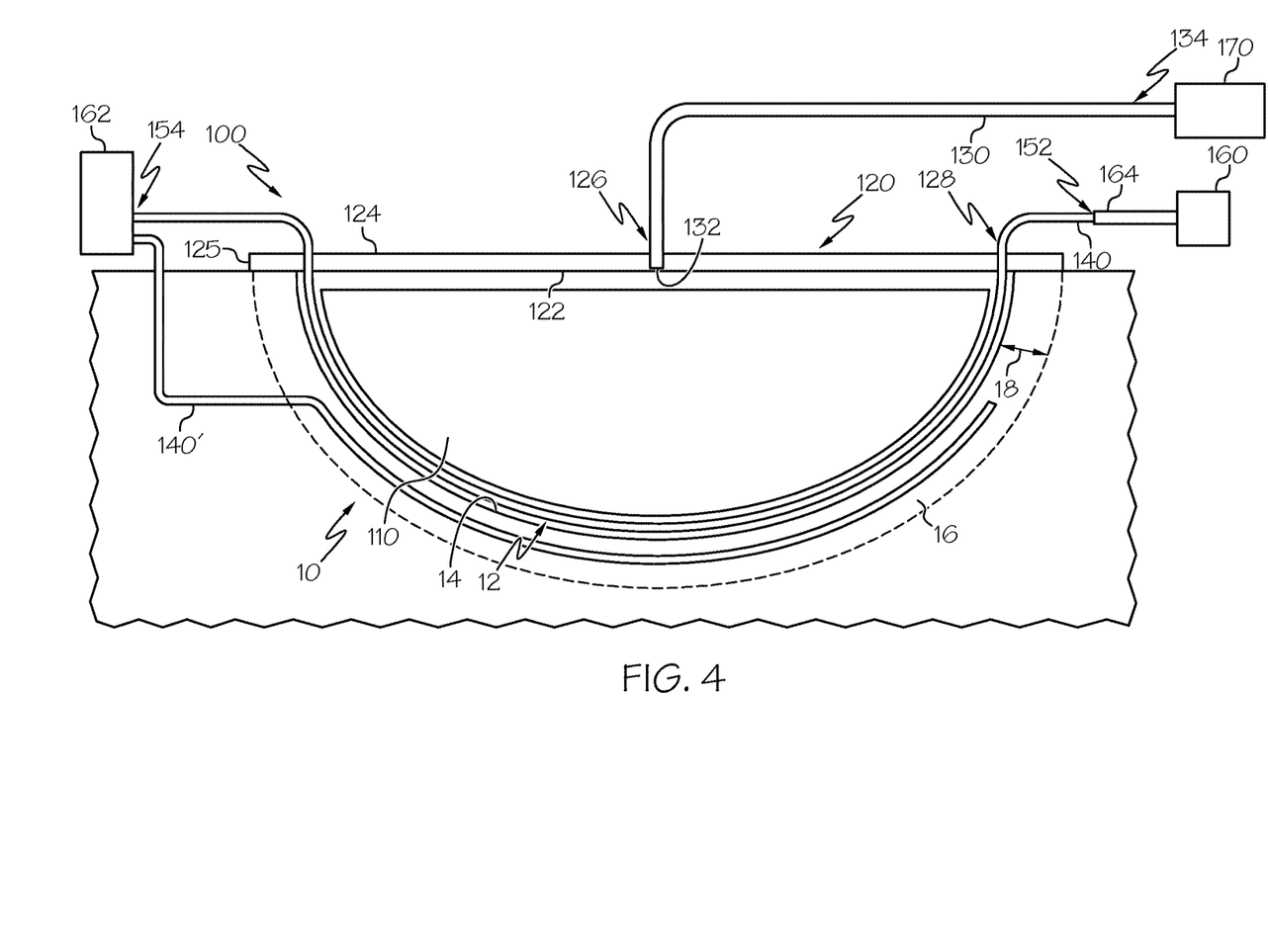
FIG. 4 is a schematic illustration of another vacuum assisted wound closure assembly having multiple light diffusing optical fibers extending into a wound, according to one or more embodiments shown and described herein.

Referring now to FIG. 4, the vacuum assisted wound closure assembly 100 may comprise a second light diffusing optical fiber 140'. The second light diffusing optical fiber 140' may be optically coupled to the therapeutic light source 160 and/or optically coupled to the second therapeutic light source 162. It should be understood that the vacuum assisted wound closure assembly 100 may comprise any number of light diffusing optical fibers 140. Moreover, the vacuum assisted wound closure assembly 100 may comprise an imaging optical fiber optically coupled to an imaging device.

Referring again to FIGS. 1-4, a method of irradiating the wound 10 using the vacuum assisted wound closure assembly 100 is contemplated. The method of irradiating the wound 10 may comprise positioning the wound insertion foam 110 within the wound cavity 12 of the wound 10 and covering the wound insertion foam 110 positioned within the wound cavity 12 using the wound sealing layer 120 such that the sealing surface 122 seals the wound insertion foam 110 within the wound cavity 12. Further, the drainage end 132 of the drain tube 130 may be positioned within or extend through the vacuum entry port 126 of the sealing surface 122 such that the drainage end 132 is fluidly coupled to the wound insertion foam 110 and the wound cavity 12. The drainage end 132 of the drain tube 130 may be sealed within the wound cavity 12 using the wound sealing layer 120. Further, the vacuum end 134 of the drain tube 130 may be fluidly coupled to a vacuum source 170, for example, directly coupled to the vacuum source 170 such that vacuum source 170 may generate suction within the drain tube 130 and pump fluid from the wound cavity 12 using the drainage end 132 of the drain tube 130.

Next, the method comprises positioning at least a portion of the treatment length of the light diffusing optical fiber 140 within the wound 10, for example, within a wound tissue region 16 of the wound 10, the wound cavity 12 of the wound 10, or both. The wound tissue region 16 comprises a portion of wound tissue extending from a wound cavity surface 14 to a wound depth 18. For example, at least a portion of the treatment length of the light diffusing optical fiber 140 may be positioned within the wound tissue region 16 at a depth less than the wound depth 18 extending from the wound cavity surface 14 such that the light diffusing optical fiber 140 may irradiate the wound tissue region 16. The light diffusing optical fiber 140 may extend into the wound tissue region 16 of the wound 10 from a location within the wound cavity 12, as depicted in FIG. 1. Alternatively, the light diffusing optical fiber 140 may extend into the wound tissue region 16 from a location apart from the wound cavity 12, for example, as depicted by the second light diffusing optical fiber 140' shown in FIG. 4.

Further, at least a portion of the treatment length of the light diffusing optical fiber 140 may be housed within the fiber housing catheter 190. For example, as depicted in FIG. 1, the fiber housing catheter 190 may house some or all of the portion of the light diffusing optical fiber 140 that is positioned within the wound tissue region 16 such that the light diffusing optical fiber 140 does not directly contact the wound tissue of the wound tissue region 16. As stated above, the fiber housing catheter 190 may comprise an optically transmissive material such that light emitted by the light diffusing optical fiber may traverse the fiber housing catheter 190.

As depicted in FIGS. 1 and 2, at least a portion of the light diffusing optical fiber 140 may be positioned between the wound insertion foam 110 and wound cavity surface 14. For example, as depicted in FIG. 1, a portion of the light diffusing optical fiber 140 may be positioned within the wound cavity 12 and a portion of the light diffusing optical fiber 140 may be positioned within the wound tissue region 16. As depicted in FIG. 2, the light diffusing optical fiber 140 may be positioned within the wound cavity 12 without extending into the wound tissue region 16. Further, at least a portion of the light diffusing optical fiber 140 may extend into the wound insertion foam 110. The termination end 154 of the light diffusing optical fiber 140 may terminate within the wound tissue region 16, may terminate within the wound cavity 12, for example, between the wound insertion foam 110 and wound cavity surface 14, or may terminate within the wound insertion foam 110. Further, the termination end 154 may terminate outside of the wound 10, for example, when the termination end 154 is coupled to the second therapeutic light source 162.

Referring again to FIGS. 1-4, the method of irradiating the wound 10 using the vacuum assisted wound closure assembly 100 further comprises emitting light from the therapeutic light source 160 optically coupled to the light diffusing optical fiber 140 such that at least a portion of light emitted by the therapeutic light source 160 enters the light diffusing optical fiber 140, scatters outward from the light diffusing optical fiber 140, and irradiates the wound tissue region 16 of the wound 10, the wound cavity surface 14 of the wound 10, or both. In operation, irradiating the wound 10, for example, the wound tissue region 16 and/or the wound cavity surface 14 may assist with a wound healing process and/or a wound sterilization process. Further, when the vacuum assisted wound closure assembly 100 comprises the second light diffusing optical fiber 140', at least a portion of the second light diffusing optical fiber 140' may be positioned within the wound tissue region 16, the wound cavity 12, or both, such that at least a portion of light emitted by the second therapeutic light source 162 enters the second light diffusing optical fiber 140', scatters outward from the second light diffusing optical fiber 140', and irradiates the wound tissue region 16, the wound cavity 12, or both.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present invention it is noted that the term "about" is utilized herein to represent the inherent degree of uncertainty that may be attributed to any quantitative comparison, value, measurement, or other representation. The term "about" is also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

The invention claimed is:

1. A method of irradiating a wound, the method comprising:
   positioning a wound insertion foam within a wound cavity of a wound;
   covering the wound insertion foam positioned within the wound cavity using a wound sealing layer comprising a sealing surface, such that the sealing surface seals the wound insertion foam within the wound cavity;

pumping fluid from the wound cavity using a drain tube comprising a drainage end fluidly coupled to the wound insertion foam and sealed within the wound cavity using the wound sealing layer and a vacuum end fluidly coupled to a vacuum source; and irradiating the wound using a light diffusing optical fiber optically coupled to a therapeutic light source, wherein:
the light diffusing optical fiber comprises one or more light scattering structures distributed along at least a treatment length of the light diffusing optical fiber; and
at least a portion of the treatment length of the light diffusing optical fiber is positioned within a wound tissue region of the wound, the wound cavity, or both, such that at least a portion of light emitted by the therapeutic light source enters the light diffusing optical fiber, scatters outward from the light diffusing optical fiber, and irradiates the wound tissue region, a wound cavity surface of the wound, or both;

wherein a vacuum entry port extends through the wound sealing layer and the drain tube extends into the vacuum entry port such that the drainage end of the drain tube is fluidly coupled to the wound insertion foam; and wherein the light diffusing optical fiber extends within the drain tube and extends through the vacuum entry port.

2. The method of irradiating a wound of claim 1, wherein at least a portion of the treatment length of the light diffusing optical fiber is positioned within the wound tissue region at a depth less than a wound depth extending from the wound cavity surface.

3. The method of irradiating a wound of claim 2, wherein at least a portion of the treatment length of the light diffusing optical fiber is housed within a fiber housing catheter such that at least a portion of the fiber housing catheter is positioned within the wound tissue region at a depth less than the wound depth extending from the wound cavity surface.

4. The method of irradiating a wound of claim 1, wherein at least a portion of the light diffusing optical fiber is positioned between the wound insertion foam and the wound cavity surface.

5. The method of irradiating a wound of claim 1, wherein the therapeutic light source comprises a light emitting diode (LED), an ultraviolet light source, or both, and emits light comprising a wavelength between about 250 nm and about 1100 nm.

6. The method of irradiating a wound of claim 1, wherein the therapeutic light source emits a pulsed light at a frequency within a treatment frequency range comprising between about 70 Hz and 80 Hz, between about 145 Hz and 155 Hz, between about 290 Hz and 300 Hz, between about 585 Hz and 595 Hz, between about 1170 Hz and about 1180 Hz, between about 2345 Hz and about 2355 Hz, or between about 4695 Hz and about 4705 Hz.

7. The method of irradiating a wound of claim 1, wherein the light diffusing optical fiber further comprises a core, a cladding layer encircling the core, and a coating layer encircling the cladding layer wherein the coating layer comprises a transparent medical grade polymer, a medical grade plastic, a plurality of photo-active sterilization molecules, a cross-linked coating, or a combination thereof.

8. The method of irradiating a wound of claim 1, wherein the light diffusing optical fiber comprises a cladding layer encircling a core and the one or more light scattering structures comprise a plurality of gas filled voids positioned within the cladding layer.

9. The method of irradiating a wound of claim 1, wherein:
the light diffusing optical fiber comprises a cladding layer encircling a core;
the one or more light scattering structures comprise a refractive coating optically coupled to the core of the light diffusing optical fiber; and
the refractive coating comprises an index of refraction that is greater than an index of refraction of the core and the cladding layer and comprises one or more light scattering particles.

10. The method of irradiating a wound of claim 1, wherein:
the light diffusing optical fiber further comprises a source end optically coupled to the therapeutic light source and a termination end opposite the source end; and
the termination end is optically coupled to a second therapeutic light source.

11. The method of irradiating a wound of claim 1, wherein a second light diffusing optical fiber is optically coupled to a second therapeutic light source, and at least a portion of the second light diffusing optical fiber is positioned within the wound tissue region, the wound cavity, or both, such that at least a portion of light emitted by the second therapeutic light source enters the second light diffusing optical fiber, scatters outward from the second light diffusing optical fiber, and irradiates the wound tissue region, the wound cavity, or both.

12. The method of irradiating a wound of claim 1, wherein a transmission optical fiber extends between and optically couples the light diffusing optical fiber to the therapeutic light source.

13. The method of irradiating a wound of claim 1, wherein an opaque layer is coupled to the wound sealing layer.

14. The method of irradiating a wound of claim 1, wherein:
a fluid collection vessel is fluidly coupled to the drain tube;
the drain tube comprises a collection branch extending from the drain tube at a branching location and terminating at the fluid collection vessel;
a fluid separating mesh is positioned within the drain tube at a location fluidly downstream from the branching location; and
the fluid separating mesh is structurally configured to inhibit non-gaseous fluid from traversing the fluid separating mesh and direct non-gaseous fluid into the collection branch.

15. A method of irradiating a wound, the method comprising:
positioning a wound insertion foam within a wound cavity of a wound;
covering the wound insertion foam positioned within the wound cavity using a wound sealing layer comprising a sealing surface, such that the sealing surface seals the wound insertion foam within the wound cavity;
pumping fluid from the wound cavity using a drain tube comprising a drainage end fluidly coupled to the wound insertion foam and sealed within the wound cavity using the wound sealing layer and a vacuum end fluidly coupled to a vacuum source; and
irradiating the wound using a light diffusing optical fiber optically coupled to a therapeutic light source, wherein:
the light diffusing optical fiber comprises one or more light scattering structures distributed along at least a treatment length of the light diffusing optical fiber; and at least a portion of the treatment length of the light diffusing optical fiber is positioned within a wound tissue region of the wound, the wound cavity, or both, such that at least a portion of light emitted by the therapeutic light source enters the light diffusing optical fiber, scatters outward from the light diffusing optical fiber, and irradiates the wound tissue region, a wound cavity surface of the wound, or both;

and wherein:

the light diffusing optical fiber comprises a source end optically coupled to the therapeutic light source and a termination end opposite the source end; and a reflector cap coupled to the termination end.

16. A method of irradiating a wound, the method comprising:

positioning a wound insertion foam within a wound cavity of a wound;

covering the wound insertion foam positioned within the wound cavity using a wound sealing layer comprising a sealing surface, such that the sealing surface seals the wound insertion foam within the wound cavity;

pumping fluid from the wound cavity using a drain tube comprising a drainage end fluidly coupled to the wound insertion foam and a vacuum end fluidly coupled to a vacuum source, the drainage end extending into a vacuum entry port that extends through the wound sealing layer such that the drainage end of the drain tube is fluidly coupled to the wound insertion foam and sealed within the wound cavity using the wound sealing layer; and irradiating the wound using a light diffusing optical fiber optically coupled to a therapeutic light source using a transmission optical fiber that extends between the light diffusing optical fiber and the therapeutic light source, wherein:

the light diffusing optical fiber comprises one or more light scattering structures distributed along at least a treatment length of the light diffusing optical fiber;

a portion of the light diffusing optical fiber extends within the drain tube and extends through the vacuum entry port; and at least a portion of the treatment length of the light diffusing optical fiber is positioned within a wound tissue region of the wound at a depth less than a wound depth extending from a wound cavity surface of the wound cavity, such that at least a portion of light emitted by the therapeutic light source enters the light diffusing optical fiber, scatters outward from the light diffusing optical fiber, and irradiates the wound tissue region of the wound.

17. A vacuum assisted wound closure assembly comprising a wound insertion foam, a wound sealing layer, a drain tube, a vacuum source, a light diffusing optical fiber, a transmission optical fiber, and a therapeutic light source, wherein:

the wound insertion foam is positionable within a wound cavity of a wound;

the drain tube comprises a drainage end fluidly coupled to the wound insertion foam and a vacuum end fluidly coupled to the vacuum source;

the transmission optical fiber is positioned between and optically coupled to the light diffusing optical fiber and the therapeutic light source, extends a transmission length, and optically couples the light diffusing optical fiber to the therapeutic light source;

the light diffusing optical fiber comprises a plurality of light scattering structures distributed along at least a treatment length of the light diffusing optical fiber; and the wound sealing layer comprises a sealing surface configured to seal the wound insertion foam, the drainage end of the drain tube, and at least a portion of the light diffusing optical fiber within the wound cavity when the wound insertion foam is positioned within the wound cavity;

wherein a vacuum entry port extends through the wound sealing layer and the drain tube extends into the vacuum entry port; and wherein at least one of the transmission optical fiber or the light diffusing optical fiber extends within the drain tube and extends through the vacuum entry port.

* * * * *

UNITED STATES PATENT AND TRADEMARK OFFICE
CERTIFICATE OF CORRECTION

PATENT NO. : 10,918,770 B2  
APPLICATION NO. : 15/203102  
DATED : February 16, 2021  
INVENTOR(S) : Edward John Fewkes et al.

Page 1 of 1

It is certified that error appears in the above-identified patent and that said Letters Patent is hereby corrected as shown below:

On the Title Page

On page 2, in Column 2, item (56), Other Publications, Line 9, delete "Would" and insert -- Wound --, therefor.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*